(12) United States Patent
Wang et al.

(10) Patent No.: US 6,486,093 B2
(45) Date of Patent: *Nov. 26, 2002

(54) VINYL ACETATE CATALYST COMPRISING METALLIC PALLADIUM AND GOLD PREPARED WITH POTASSIUM AURATE

(75) Inventors: Tao Wang, Corpus Christi, TX (US); Jerry A. Broussard, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/933,214

(22) Filed: Aug. 20, 2001

(65) Prior Publication Data

US 2002/0013220 A1 Jan. 31, 2002

Related U.S. Application Data

(62) Division of application No. 09/088,978, filed on Jun. 2, 1998, now Pat. No. 6,350,900.

(51) Int. Cl.⁷ ............................ B01J 23/58; B01J 23/52; B01J 23/56
(52) U.S. Cl. ................ 502/330; 502/300; 502/325
(58) Field of Search ................... 502/300, 325, 502/330

(56) References Cited

U.S. PATENT DOCUMENTS

| | | | | |
|---|---|---|---|---|
| 3,950,400 A | * | 4/1976 | Fernholz et al. | 502/330 |
| 4,093,559 A | * | 6/1978 | Fernholz et al. | 502/170 |
| 5,332,710 A | * | 7/1994 | Nicolau et al. | 502/240 |
| 5,691,267 A | * | 11/1997 | Nicolau et al. | 502/330 |
| 5,700,753 A | * | 12/1997 | Wang et al. | 502/325 |
| 6,015,769 A | * | 1/2000 | Wang | 502/325 |

* cited by examiner

Primary Examiner—Elizabeth D. Wood
(74) Attorney, Agent, or Firm—M. Susan Spiering

(57) ABSTRACT

A catalyst for the production of vinyl acetate by reaction of ethylene, oxygen and acetic acid comprising a porous support on the porous surfaces of which is deposited catalytically effective amounts of metallic palladium and gold, said catalyst having been prepared by steps comprising impregnating a porous support, the porous surfaces of which contain a catalytically effective amount of a prereduced metallic palladium, with a solution of potassium aurate, and reducing the potassium aurate to a catalytically effective amount of metallic gold. Alternate embodiments are also disclosed.

11 Claims, No Drawings

US 6,486,093 B2

VINYL ACETATE CATALYST COMPRISING METALLIC PALLADIUM AND GOLD PREPARED WITH POTASSIUM AURATE

This application is a divisional of application Ser. No. 09/088,978, filed Jun. 2, 1998 and now U.S. Pat. No. 6,350,900.

BACKGROUND OF THE INVENTION

1. Field of the Invention

This invention relates to new and improved catalysts for the production of vinyl acetate by reaction of ethylene, oxygen and acetic acid.

2. Background Information Including Description of Related Art

It is known to produce vinyl acetate by reaction of ethylene, oxygen and acetic acid using a catalyst consisting of metallic palladium and gold supported on a carrier. While the process utilizing such a catalyst is capable of producing vinyl acetate at fair levels of productivity, such productivity levels are limited by the production of undesirable by-products, particularly carbon dioxide. Thus, any expedient capable of achieving reduced production of by-products such as carbon dioxide, expressed as lower percent $CO_2$ selectivity, is very desirable.

The foregoing catalysts comprising metallic palladium and gold are conventionally prepared by a process including the steps of impregnating a porous support with a single aqueous solution or separate solutions of water-soluble salts of palladium and gold, reacting the impregnated water-soluble salts with an appropriate alkaline compound e.g., sodium hydroxide, to "fix" the palladium and gold as water-insoluble compounds, e.g. the hydroxides, and reducing the water insoluble compounds, e.g., with ethylene or hydrazine, to convert the palladium and gold to free metallic form. This type of process has the disadvantage of requiring several steps, sometimes including at least two "fixing" steps.

The following references may be considered material to the invention claimed herein.

U.S. Pat. No. 5,332,710, issued Jul. 26, 1994, to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution to precipitate such compounds, and subsequently reducing the compounds to free metallic form.

British Patent No. 1,188,777, published Apr. 22, 1970 discloses a process for the simultaneous production of an unsaturated carboxylic acid ester, e.g. vinyl acetate, from an olefin, carboxylic acid, and oxygen, and the corresponding carboxylic acid, e.g., acetic acid, from its aldehyde, using a single supported catalyst containing a palladium compound, e.g. an oxide or salt, with one or more compounds of any of various metals, e.g. metallic gold or a gold compound such as potassium aurate.

U.S. Pat. No. 5,700,753 discloses vinyl acetate (VA) catalyst prepared by adding organometallic gold complexes to prereduced palladium catalyst prepared from $Na_2PdCl_4$. The organometallic gold compound does not require a fixing procedure.

SUMMARY OF THE INVENTION

In accordance with this invention, a catalyst is provided useful for the production of vinyl acetate (VA) by reaction of ethylene, oxygen and acetic acid with low carbon dioxide selectivity, said catalyst being prepared by steps comprising impregnating a porous support, the porous surfaces of which contain a catalytically effective amount of prereduced metallic palladium, with a solution of potassium aurate, $KAuO_2$, and reducing the potassium aurate to a catalytically effective amount of metallic gold. The use of such catalyst often results in lower carbon dioxide and heavy ends selectivities, which are usually accompanied by a higher vinyl acetate productivity, than when various conventional catalysts comprising metallic palladium and gold are employed.

DETAILED DESCRIPTION OF THE INVENTION

Disclosed herein is a process to prepare catalyst useful in the production of VA. Prereduced Pd catalyst were prepared by the impregnation of a support with aqueous solution of $Na_2PdCl_4$ followed by fixing with NaOH and reduction of the Pd. A thin shell Pd catalyst was obtained, to which was then contacted with a solution of aqueous $KAuO_2$ to form a second shell of Au on the support. Ultimately, a shell catalyst of Pd and Au was formed wherein a fixing step for the Au was not necessary. The Pd and Au were distributed as a thin metal shell on the support structure.

As an alternative embodiment, the catalyst may be prepared by first contacting the support with $KAuO_2$, followed by contact with $Na_2PdCl_4$. The Pd compound may then be fixed with a precipitating solution such as NaOH, and the Au and Pd reduced with a reducing agent. Alternatively, the Au may be reduced before the addition of the Pd solution.

A still further embodiment of the inventive procedure involves use of sodium-free reagents; such as described in U.S. Pat. No. 5,693,586.

The support material in the catalyst of this invention is composed of particles having any of various regular or irregular shapes, such as spheres, tablets, cylinders, rings, stars, or other shapes, and may have dimensions such as diameter, length or width of about 1 to about 10 mm., preferably about 3 to 9 mm. Spheres having a diameter of about 4 to about 8 mm. are preferred. The support material may be composed of any suitable porous substance, e.g., silica, alumina, silica-alumina, titania, zirconia, silicates, aluminosilicates, titanates, spinel, silicon carbide, carbon, and the like.

The support material may have a surface area within the range, for example, of about 10 to about 350, preferably about 100 to about 200 $m^2/g$, an average pore size in the range, for example, of about 50 to about 2000 angstroms, and a pore volume in the range, for example, of about 0.1 to about 2, preferably about 0.4 to about 1.2 ml/g.

In the preparation of the catalyst used in the process of this invention, the support material is first treated to deposit a catalytic amount of palladium on the porous surfaces of the support particles. Any of various methods for accomplishing this purpose may be used, all of which involve the impregnation of the support with an aqueous solution of a water-soluble compound of palladium. Palladium(II) chloride, sodium palladium(II) chloride (i.e., sodium tetrachloropalladium(II), $Na_2PdCl_4$), potassium palladium (II) chloride, palladium(II) nitrate or palladium(II) sulfate are examples of suitable water-soluble palladium compounds. Sodium tetrachloropalladium(II) is the preferred salt for impregnation because of its good water solubility. The impregnation can be accomplished by the "incipient wetness" method wherein an amount of water-soluble metal compound solution used for the impregnation is from about 95 to about 100 percent of the absorptive capacity of the support material. The concentration of the solution is such that the amount of elemental palladium in the solution absorbed on the support is equal to a desired predetermined amount. The impregnation is such as to provide, for example, about 1 to about 10 grams of elemental palladium per liter of finished catalyst.

After the impregnation of the support with an aqueous solution of water-soluble salt of palladium, the palladium is "fixed", i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkali metal in the alkaline compound should be in an amount of, for example, about 1 to about 2, preferably about 1.1 to about 1.8 times the amount necessary to react with the catalytically active cations present in the water-soluble salt. The fixing of the palladium may be done by the incipient wetness method wherein the impregnated support is dried, e.g., at a temperature of 150° C. for one hour, contacted with an amount of solution of the alkaline material equal to about 95–100% of the pore volume of the support, and allowed to stand for a period of about ½ to about 16 hours; or the roto-immersion method wherein the impregnated support without drying is immersed in a solution of the alkaline material and is rotated and/or tumbled during at least the initial period of precipitation such that a thin band of the precipitated water-soluble compound is formed at or near the surface of the support particles. The rotation and tumbling may be carried out, for example, at about 1 to about 10 rpm for a period, e.g., of at least about 0.5 hour, preferably about 0.5 to about 4 hours. The contemplated roto-immersion method is disclosed in U.S. Pat. No. 5,332,710, the entire disclosure of which is incorporated herein by reference.

The fixed, i.e., precipitated palladium compound may then be reduced, for example, in the vapor phase with ethylene, e.g., 5% in nitrogen at 150° C. for 5 hours, after first washing the catalyst containing the fixed palladium compounds until it is free of anions such as halide, and drying, e.g., at 150° C. overnight under constant $N_2$ purge, or such reduction may be accomplished in the liquid phase at room temperature with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed palladium compound present on the support may be employed as conventional in the art. The reduction of the fixed palladium compound mainly results in the formation of the free metal, although a minor amount of metal oxide may also be present.

After the catalyst containing palladium in free metallic form deposited on a support material is prepared by any of the foregoing methods, it is impregnated with an aqueous solution of potassium aurate, preferably by incipient wetness. The catalyst is then dried such that the catalyst contains potassium aurate in an amount sufficient to provide, for example, about 0.5 to about 10 grams of elemental gold per liter of finished catalyst, with the amount of gold being from about 10 to about 125 wt. % based on the weight of palladium present. The potassium aurate is then reduced to metallic gold using any of the techniques described previously for the reduction of palladium from the "fixed", i.e., water insoluble, palladium compound on the surface of the support. Such reduction of potassium aurate is carried out without any necessity for the intermediate steps of fixing the gold on the support as a water-insoluble compound and washing such compound until chlorine-free, as described previously for palladium and as ordinarily required for gold in the preparation of vinyl acetate catalysts comprising palladium and gold. The elimination of such fixing and washing steps in connection with gold is an important advantage in the preparation of the catalyst of this invention. A high gold metal retention catalyst was obtained by this method. The catalyst also contains Pd and Au distributed in a thin shell at or near the surface of the catalyst support.

One of the problems in producing VA catalysts has been low noble metal retention on the catalyst support. The use of $KAuO_2$ precursors offer a method to produce salt-free, highly dispersed metallic particle catalysts, with no fixing step involved for the Au complexes. An advantage of no fixing step for the Au complexes is the increased gold retention since Au is partially washed out of the catalyst during the fixing/washing step under prior art techniques, and increased Au/Pd ratio on the catalyst.

Although the catalysts of this invention have been described primarily in connection with those containing only palladium and gold as catalytically active metals, the catalyst may also contain one or more additional catalytically active metallic elements in the form of the free metal, oxide, or mixture of free metal and oxide. Such metallic elements may be, for example, copper, magnesium, calcium, barium, zirconium and/or cerium. When a metal in addition to palladium and gold is desired in the catalyst, the support may usually be impregnated with a water soluble salt of such metal dissolved in the same impregnating solution as that containing the water-soluble palladium salt. The support may thus be simultaneously impregnated with water-soluble salts of palladium and the additional metal which are then simultaneously fixed and reduced in the same manner as described previously for palladium alone. The catalyst containing the palladium as the free metal and an additional metal as the oxide and/or free metal is then impregnated with potassium aurate which is then reduced to gold as free metal without an intermediate fixing step as described previously in connection with palladium as the only other metal in addition to gold.

Advantageously, the catalyst containing palladium and gold in free metallic form may optionally be impregnated with a solution of an alkali metal acetate, preferably potassium or sodium acetate, and most preferably potassium acetate (KOAc). After drying, the finished catalyst may contain, for example, about 10 to about 70, preferably about 20 to about 60 grams of alkali metal acetate per liter of finished catalyst. Optimally, $KAuO_2$ may be added together with KOAc in one step to the prereduced Pd catalyst.

When vinyl acetate is prepared using the catalyst of the present invention, a stream of gas, which contains ethylene, oxygen or air, acetic acid, and desirably an alkali metal acetate, is passed over the catalyst. The composition of the gas stream can be varied within wide limits, taking in account explosive limits. For example, the molar ratio of ethylene to oxygen can be about 80:20 to about 98:2, the molar ratio of acetic acid to ethylene can be about 2:1 to about 1:10, preferably about 1:2 to 1:5, and the content of gaseous alkali metal acetate can be about 1 to about 100 ppm based on the weight of acetic acid employed. The gas stream also can contain other inert gases, such as nitrogen, carbon dioxide and/or saturated hydrocarbons. Reaction temperatures which can be used are elevated temperatures, preferably those in the range of about 150–220° C. The pressure employed can be a somewhat reduced pressure, normal pressure or elevated pressure, preferably a pressure of up to about 20 atmospheres gauge.

The following examples further illustrates the invention.

Examples 1 to 10

These examples illustrate the preparation of catalysts under this invention containing varying amounts of palladium and gold in free metallic form A support material containing prereduced palladium metal was prepared as follows:

A support material in an amount of 250 ml consisting of Sud Chemie KA-160 silica spheres having a nominal diameter of 7 mm., a surface area of about 160 to 175 m²/g, and a pore volume of about 0.68 ml/g., was first impregnated by incipient wetness with 82.5 ml of an aqueous solution of sodium tetrachloropalladium (II) ($Na_2PdCl_4$) sufficient to provide about 7 grams of elemental palladium per liter of catalyst. The support was shaken in the solution for 5 minutes to ensure complete absorption of the solution. The palladium was then fixed to the support as palladium(II) hydroxide by contacting the treated support by roto-immersion for 2.5 hours at approximately 5 rpm with 283 ml of an aqueous sodium hydroxide solution prepared from 50% w/w $NaOH/H_2O$ in an amount of 120% of that needed to convert the palladium to its hydroxide. The solution was drained from the treated support which was then washed with deionized water until chloride free (about 5 hours) and dried overnight at 150° C. under constant nitrogen purge. The palladium was then reduced to the free metal by contacting the support with ethylene (5% in nitrogen) in the vapor phase at 150° C. for 5 hours, or with, hydrazine at room temperature for 4 hours followed by washing with deionized water for 2 hours and drying in an oven at 150° C. for 5 hours, to obtain a support containing a nominal amount of 7 gliter (g/l) of prereduced Pd.

In the production of potassium aurate utilized to impregnate the support with gold, auric hydroxide, $Au(OH)_3$ was first prepared by mixing 300 g of sodium tetrachlorogold (III), $NaAuCl_4$, containing 0.20 g Au/g solution with 73.6 g of a 50% w/w $NaOH/H_2O$ dissolved in 200 ml deionized water. An excess of NaOH was added to bring the pH to about 8 and the solution was stirred and heated to 60° C. for 3 hours to form an orange precipitate. Filtration yielded on orange solid which was washed with deionized water until chloride free and dried in a vacuum oven at 50° C. in a flow of $N_2$ to obtain an orange red solid of $Au(OH)_3$. Analysis of the solid indicated a gold content of 79.5% of gold which agrees with the calculated value.

Auric hydroxide in an amount of 0.5 gram was mixed with 0.12 gram of KOH in 35 ml of water, and the resulting orange suspension was heated to 82 to 85° C. and stirred at this temperature until all solids were dissolved to yield a clear yellow solution of potassium aurate as ($KAuO_2$). This solution was added to 100 ml of support containing a nominal amount of 7 g/l of prereduced Pd prepared as described previously using ethylene as reducing agent. The impregnation was conducted for about 25–30 min. The catalyst was dried in an oven at 100° C. for 5 hours in a flow of $N_2$ purge. The gold in the treated catalyst was then reduced by 5% ethylene in $N_2$ at 120° C. for 5 hours to obtain free metallic gold on the support.

Finally the catalyst was impregnated by incipient wetness with an aqueous solution of 4 g of potassium acetate in 33 ml $H_2O$ and dried in a fluid bed drier at 100° C. for 1.5 hour.

The foregoing description of the preparation of a catalyst in accordance with this invention is specific to the catalysts of Examples 1, 2 and 3 which contain the nominal amounts, i.e., corresponding to the concentrations and amounts of the impregnating solutions, of 7 grams of Pd and 4 grams of Au per liter of catalyst, and in which the Pd and Au are both reduced with ethylene. However, the catalysts of Examples 4 to 10 which contain a different amount of Pd and/or Au are similarly prepared except that the concentration or amount of the $Na_2PdCl_4$ and/or $KAuO_2$ impregnating solution is changed to obtain the desired nominal amounts of Pd and/or Au on the support, and the reduction of Pd and Au is each accomplished with ethylene and/or hydrazine, as previously described. The reducing agent used in the preparation ($C_2H_4$ and/or $N_2H_4$), the nominal amounts of Pd and Au corresponding to the concentrations and amounts of impregnating solutions (Nom. Amt., g/l), and actual amounts of Pd and Au on the catalysts of Examples 1–10 determined by analysis and % metal retention are shown in Table I. In Example 7, the entry in the table of "$N_2H_4$, $C_2H_4$" indicates that the Pd was prereduced with hydrazine and the Au was reduced in the potassium aurate was reduced with ethylene, while the entry "$C_2H_4$, $N_2H_4$" in Example 10 indicates that the Pd was prereduced with ethylene and the Au with hydrazine as previously described.

The catalysts of the examples were tested for their activity and selectivity to various by-products in the production of vinyl acetate by reaction of ethylene, oxygen and acetic acid. To accomplish this, about 60 ml of the catalyst prepared as described were placed in a stainless steel basket with the temperature capable of being measured by a thermocouple at both the top and bottom of the basket. The basket was placed in a Berty continuously stirred tank reactor of the recirculating type and was maintained at a temperature which provided about 45% oxygen conversion with an electric heating mantle. A gas mixture of about 50 normal liters (measured at N.T.P.) of ethylene, about 10 normal liters of oxygen, about 49 normal liters of nitrogen, about 50 g of acetic acid, and about 4 mg of potassium acetate, was caused to travel under pressure at about 12 atmospheres through the basket, and the catalyst was aged under these reaction conditions for at least 16 hours prior to a two hour run, after which the reaction was terminated. Analysis of the products was accomplished by on-line gas chromatographic analysis combined with off-line liquid product analysis by condensing the product stream at about 10° C. to obtain optimum analysis of the end products vinyl acetate (VA), carbon dioxide ($CO_2$), vinyl acetate (VA), heavy ends (HE) and ethyl acetate (ETOAc), the results of which were used to calculate the selectivities of these materials based on ethylene for each example as shown in Table I. The relative activity of the reaction expressed as an activity factor (Activity) is also shown in Table I and is computer calculated. The computer program uses a series of equations that correlates the activity factor with the catalyst temperature (during the reaction), oxygen conversion, and a series of kinetic parameters for the reactions that take place during VA synthesis. More generally, the activity factor is inversely related to the temperature required to achieve constant oxygen conversion.

TABLE I

| | | Metal Content of Catalyst | | | | | | | | |
|---|---|---|---|---|---|---|---|---|---|---|
| | Red. | Nom. Amt g/l | | Actual Amt g/l | | Pd/Au % metal retention | | | % Selectivity | |
| Ex. | Agent | Pd | Au | Pd | Au | Pd | Au | Activity | $CO_2$ | HE | ETOAc |
| 1 | $C_2H_4$ | 7 | 4 | 6.23 | 3.44 | 89 | 86 | 1.96 | 8.3 | 1.407 | 0.058 |
| 2 | $C_2H_4$ | 7 | 4 | 6.93 | 4.00 | 99 | 100 | 2.13 | 9.10 | 1.436 | 0.049 |
| 3 | $C_2H_4$ | 7 | 4 | 6.65 | 4.44 | 95 | 112 | 2.1 | 8.6 | 1.256 | 0.059 |
| 4 | $N_2H_4$ | 7 | 4 | 5.25 | 3.48 | 75 | 87 | 1.89 | 8.68 | 1.005 | 0.082 |
| 5 | $C_2H_4$ | 7 | 5 | 7.00 | 4.00 | 100 | 80 | 2.18 | 9.00 | 1.459 | 0.078 |
| 6 | $N_2H_4$ | 7 | 5 | 6.30 | 4.75 | 90 | 95 | 2.08 | 8.8 | 0.997 | 0.105 |
| 7 | $N_2H_4$ $C_2H_4$ | 7 | 5 | 6.65 | 5.00 | 95 | 100 | 1.78 | 11.57 | 0.636 | 0.151 |
| 8 | $C_2H_4$ | 8 | 4.57 | 8.00 | 4.34 | 100 | 95 | 2.37 | 9.45 | 1.549 | 0.061 |
| 9 | $N_2H_4$ | 8 | 4.57 | 7.60 | 4.25 | 95 | 93 | 2.09 | 8.95 | 1.229 | 0.108 |
| 10 | $C_2H_4$ $N_2H_4$ | 8 | 5.57 | 7.84 | 5.18 | 98 | 93 | 2.51 | 9.54 | 1.462 | 0.082 |

The values shown in Table I indicate that the catalysts of this invention in many instances can be used to synthesize vinyl acetate by reaction of ethylene, oxygen, and acetic acid with lower $CO_2$ and heavy ends selectivities than various conventional and/or commercial catalysts comprising palladium and gold, while maintaining equivalent levels of activity.

What is claimed is:

1. A method of preparing a catalyst for the production of vinyl acetate by reaction of ethylene, oxygen and acetic acid comprising impregnating a porous support, the porous surfaces of which contain a catalytically effective amount of prereduced palladium with a solution of potassium aurate, and reducing the potassium aurate to a catalytically effective amount of metallic gold.

2. The method of claim 1 wherein said support containing prereduced palladium is prepared by steps comprising impregnating a porous support with an aqueous solution of a water-soluble palladium salt, fixing said palladium as a water-insoluble compound by reaction with an appropriate alkaline compound, and reducing to its free metallic state the water-insoluble compound of palladium present on the support.

3. The method of claim 2 wherein said water-soluble palladium salt is sodium tetrachloropalladium(II), $Na_2PdCl_4$.

4. The method of claim 1 wherein said porous support contains about 1 to about 10 grams of palladium, and about 0.5 to about 10 grams of gold per liter of catalyst, with the amount of gold being from about 10 to about 125 wt. % based on the weight of palladium.

5. The method of claim 1 wherein said catalyst is impregnated with a solution of an alkali metal acetate.

6. The method of claim 5 wherein said alkali metal acetate is potassium acetate which is deposited on the catalyst in an amount of about 10 to about 70 grams/liter of catalyst.

7. The method of claim 5 wherein the acetate and aurate are added in one step.

8. The method of claim 1 prepared with sodium-free reagents.

9. The method of claims 1 wherein the Pd and Au forms a shell at or near the surface of the support.

10. A method of preparing a catalyst for production of vinyl acetate comprising impregnating a porous support with potassium aurate, followed by contacting with a solution of water-soluble palladium salt, fixing said palladium solution as a water-insoluble compound and. reducing the gold and palladium to their metallic form.

11. The method of claim 10 wherein the gold may be reduced before the addition of the palladium solution the support.

* * * * *